(12) United States Patent
Kim et al.

(10) Patent No.: US 12,083,225 B2
(45) Date of Patent: Sep. 10, 2024

(54) SOLVENT REMOVING APPARATUS AND METHOD OF PRODUCING MICROSPHERE USING THE SAME

(71) Applicant: Inventage Lab Inc., Gyeonggi-do (KR)

(72) Inventors: Ju Hee Kim, Gyeonggi-do (KR); Chan Hee Chon, Gyeonggi-do (KR)

(73) Assignee: INVENTAGE LAB INC., Gyeonggi-do (KR)

( * ) Notice: Subject to any disclaimer, the term of this patent is extended or adjusted under 35 U.S.C. 154(b) by 0 days.

(21) Appl. No.: 18/038,589

(22) PCT Filed: Dec. 3, 2021

(86) PCT No.: PCT/KR2021/018252
§ 371 (c)(1),
(2) Date: May 24, 2023

(87) PCT Pub. No.: WO2022/139242
PCT Pub. Date: Jun. 30, 2022

(65) Prior Publication Data
US 2023/0346707 A1 Nov. 2, 2023

(30) Foreign Application Priority Data
Dec. 24, 2020 (KR) ........................ 10-2020-0182709

(51) Int. Cl.
*A61K 9/16* (2006.01)
*B01D 17/04* (2006.01)
*B01D 35/027* (2006.01)

(52) U.S. Cl.
CPC ............ *A61K 9/1694* (2013.01); *B01D 17/04* (2013.01); *B01D 35/027* (2013.01)

(58) Field of Classification Search
None
See application file for complete search history.

(56) References Cited

U.S. PATENT DOCUMENTS

2010/0187186 A1 7/2010 Howdeshell et al.
2011/0250264 A1* 10/2011 Schutt .................. A61K 9/1277
239/11

FOREIGN PATENT DOCUMENTS

| CA | 2937235 A1 * | 9/2016 | ............ C10G 1/045 |
| JP | H11-505250 A | 5/1999 | |
| JP | 2008-523972 A | 7/2008 | |
| JP | 2013-531549 A | 8/2013 | |
| JP | 2017-523128 A | 8/2017 | |

(Continued)

OTHER PUBLICATIONS

Office action issued on Dec. 12, 2023 from Japan Intellectual Property Office in a counterpart Japanese Patent Application No. 2023-535702( all the cited references are listed in this IDS.) (English translation is also submitted herewith.).

(Continued)

*Primary Examiner* — Jeffrey D Washville
(74) *Attorney, Agent, or Firm* — The PL Law Group, PLLC

(57) ABSTRACT

A solvent-removing apparatus according to an embodiment includes a tank body accommodating an emulsion including first source material in a continuous phase and second source material in a dispersed phase, a fluid supply unit for supplying fluid into the tank body to cause the emulsion to circulate, and a discharge unit for discharging the gas in the tank body to the outside.

9 Claims, 3 Drawing Sheets

(56) References Cited

FOREIGN PATENT DOCUMENTS

| | | |
|---|---|---|
| KR | 10-2005-0109384 A | 11/2005 |
| KR | 10-0681213 B1 | 2/2007 |
| KR | 10-2008-0045210 A | 5/2008 |
| KR | 10-2017-0026625 A | 3/2017 |
| KR | 10-2019-0084276 A | 7/2019 |
| KR | 10-2010573 B1 | 8/2019 |
| KR | 10-2283250 B1 | 7/2021 |
| WO | WO 2004/024056 A1 | 3/2004 |

OTHER PUBLICATIONS

International Search Report for PCT/KR2021/018252 mailed on Mar. 10, 2022.

Office action issued on Apr. 26, 2021 from Korean Patent Office in a counterpart Korean Patent Application No. 10-2020-0182709 (all the cited references are listed in this IDS.) (English translation is also submitted herewith.).

Notice of Allowance issued on Jul. 2, 2021 from Korean Patent Office in a counterpart Korean Patent Application No. 10-2020-0182709 (all the cited references are listed in this IDS.) (English translation is also submitted herewith.).

\* cited by examiner

SOLVENT REMOVING APPARATUS AND METHOD OF PRODUCING MICROSPHERE USING THE SAME

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2021/018252, filed Dec. 3, 2021, which claims priority to the benefit of Korean Patent Application No. 10-2020-0182709 filed in the Korean Intellectual Property Office on Dec. 24, 2020, the entire contents of which are incorporated herein by reference.

BACKGROUND

1. Technical Field

The present invention relates to a solvent removing apparatus and a method of producing a microsphere by using the solvent removing apparatus, and more particularly, to a solvent removing apparatus for extracting and removing a solvent of an emulsion used for producing a microsphere, and a method of producing a microsphere by using the solvent removing apparatus.

2. Background Art

One of the drug delivery systems that are currently being actively researched, developed, and utilized is the so-called Polymeric Drug-Delivery System (PDDS), which controllably releases the fixed amount of a therapeutic agent to both hydrophilic or hydrophobic therapeutic agents in circulating doses over an extended period of time by using biodegradable, biocompatible and non-toxic polymers, for example, polylactic acid (PLA)/polyglycolic (PGA) polymers.

The biodegradable polymer may be prepared in the form of microspheres by various known techniques. In the preparation of these biodegradable polymer microspheres, the most frequently used method is dissolving the biodegradable polymer or the material to be encapsulated with the biodegradable polymer (pharmaceutical or other active agent) in a solvent by using a known method, and dispersing or emulsifying the dissolved polymer in an aqueous solution containing a surfactant. Subsequently, the solvent is removed from the microsphere and dried to obtain a microsphere product. In the microsphere producing process according to the known technology, a toxic solvent, such as dichloromethane or chloroform, is mainly used to dissolve the biodegradable polymer and the active agent, and sufficient time and effort need be devoted to the removal of the solvent so that these solvents do not remain in the microsphere product that is the final product, thereby increasing the time to obtain the microsphere product, and acting as a hindrance to mass production. Accordingly, efforts have been made to mass-produce high-quality microspheres at low cost.

In particular, technologies related to various solvent removing apparatuses for removing a solvent have been developed, most of the apparatuses are the apparatuses for extracting and removing a solvent by stirring an emulsion by using a physical rotational motion by using an impeller or a stirrer coupled to a shaft rotating by using a motor.

SUMMARY

The present invention has been made in an effort to solve the problems in the related art, and provides a solvent removing apparatus which efficiently extracts and removing a solvent from a dispersed phase of an emulsion used for producing a microsphere and has a simple configuration.

The present invention has also been made in an effort to solve the problems in the related art, and provides a method of producing a microsphere by using the solvent removing apparatus.

According to an exemplary embodiment of the inventive concept, an apparatus for removing a solvent includes a tank body configured to accommodate an emulsion including a first raw material of a continuous phase and a second raw material of a dispersed phase, a fluid supply part configured to supply a fluid into the tank body and form a flow in the emulsion, and an exhaust part configured to discharge gas inside the tank body to the outside of the tank body. The fluid supply part includes a first fluid supply part and a second fluid supply part. The first fluid supply part and the second fluid supply part are disposed while being spaced apart from each other inside the tank body, so that a rotational flow is formed in the emulsion by the fluid supplied through the first fluid supply part and the second fluid supply part.

In an exemplary embodiment, the fluid supply part may supply gas bubbles to the emulsion accommodated inside the tank body.

In an exemplary embodiment, the first fluid supply part and the second fluid supply part may supply the fluids in different directions. The tank body may have a bottom portion formed on a plane formed by a first direction and a second direction perpendicular to the first direction, and a lateral wall portion extended in a third direction perpendicular to the first direction and the second direction. The first fluid supply part and the second fluid supply part may be spaced apart from each other in the first direction, be spaced apart from each other in the second direction, and be spaced apart from each other in the third direction.

In an exemplary embodiment, the exhaust part may suck in the gas inside the tank body and depressurizes the inside of the tank body.

In an exemplary embodiment, the apparatus may further include a liquid supply part configured to supply a liquid into the tank body. The liquid may include a main ingredient of the continuous phase.

In an exemplary embodiment, the apparatus may further include a liquid discharge part configured to discharge a part of the continuous phase of the emulsion inside the tank body to the outside of the tank body.

According to an exemplary embodiment of the inventive concept, an apparatus for removing a solvent includes a tank body configured to accommodate an emulsion including a first raw material of a continuous phase and a second raw material of a dispersed phase, a fluid supply part configured to supply a fluid into the tank body and form a flow in the emulsion, an exhaust part configured to discharge gas inside the tank body to the outside of the tank body, and a liquid discharge part configured to discharge a part of the continuous phase of the emulsion inside the tank body to the outside of the tank body. The liquid discharge part has a pipe portion extended into the tank body and an expanded pipe portion connected to a distal end of the pipe portion. The expanded pipe portion is located at a first height from a bottom portion of the tank body, and is in contact with a water level surface of the emulsion to maintain an appropriate volume of the emulsion inside the tank body.

In an exemplary embodiment, a filter may be formed in the expanded pipe portion, so that only the continuous phase of the emulsion passes through the filter and the dispersed phase of the emulsion or microspheres solidified from the dispersed phase do not pass through the filter.

In an exemplary embodiment, the first raw material may include purified water and surfactant, and the second raw material includes an organic solvent, a biodegradable polymer, and a drug.

In an exemplary embodiment, the apparatus may further include a heating part configured to heat the emulsion inside the tank body.

According to an exemplary embodiment of the inventive concept, a method of producing a microsphere by using a solvent removing apparatus including a tank body, a fluid supply part for supplying a fluid into the tank body, and an exhaust part for discharging gas inside the tank body to the outside of the tank body, includes preparing a first raw material, and preparing a second raw material including a biodegradable polymer, a drug, and a solvent, forming an emulsion including the first raw material of a continuous phase and the second raw material of a dispersed phase by using the first raw material and the second raw material, and extracting and removing the solvent from the dispersed phase of the emulsion by using the solvent removing apparatus to form a microsphere.

In an exemplary embodiment, the fluid supply part may form a rotational flow in the emulsion by supplying gas bubbles to the emulsion accommodated in the tank body.

In an exemplary embodiment, the solvent removing apparatus may further include a liquid supply part for supplying a liquid into the tank body, and a liquid discharge part for discharging a part of the continuous phase of the emulsion inside the tank body to the outside of the tank body. In the forming of the microsphere, the liquid may be supplied into the tank body, the liquid may include a main ingredient of the continuous phase, and a water level surface of the emulsion may be maintained with a predetermined appropriate water level surface by discharging a part of the continuous phase of the emulsion inside the tank body to the outside of the tank body.

In an exemplary embodiment, the first raw material may include purified water and a surfactant. The solvent of the second raw material may be an organic solvent.

According to the present exemplary embodiment, the solvent removing apparatus includes a fluid supply part which supplies a fluid into the tank body to form a flow in the emulsion, and an exhaust part which discharges the gas inside the tank body to the outside of the tank, thereby easily extracting and evaporating the solvent even without an impeller or stirrer structure coupled to a shaft rotated by using a motor. Accordingly, the solvent removing apparatus has a simpler configuration that that of the structure in the related art, and may have an advantageous operation effect in sealing and the like for washing and sterilizing the inside of the tank body.

Further, the solvent removing apparatus further includes the liquid supply part which supplies the liquid into the tank body and the liquid discharge part which discharges some of the continuous phase of the emulsion inside the tank body to the outside of the tank body, so that the solvent may be efficiently and continuously extracted and evaporated. Through this, it is possible to provide the efficient microsphere producing method by omitting or minimizing the subsequent separate filtering and cleaning operations after the solvent removing operation.

However, the effects of the present invention are not limited to the above effects, and may be variously expanded without departing from the spirit and scope of the present invention.

DETAILED DESCRIPTION

Figure 1:
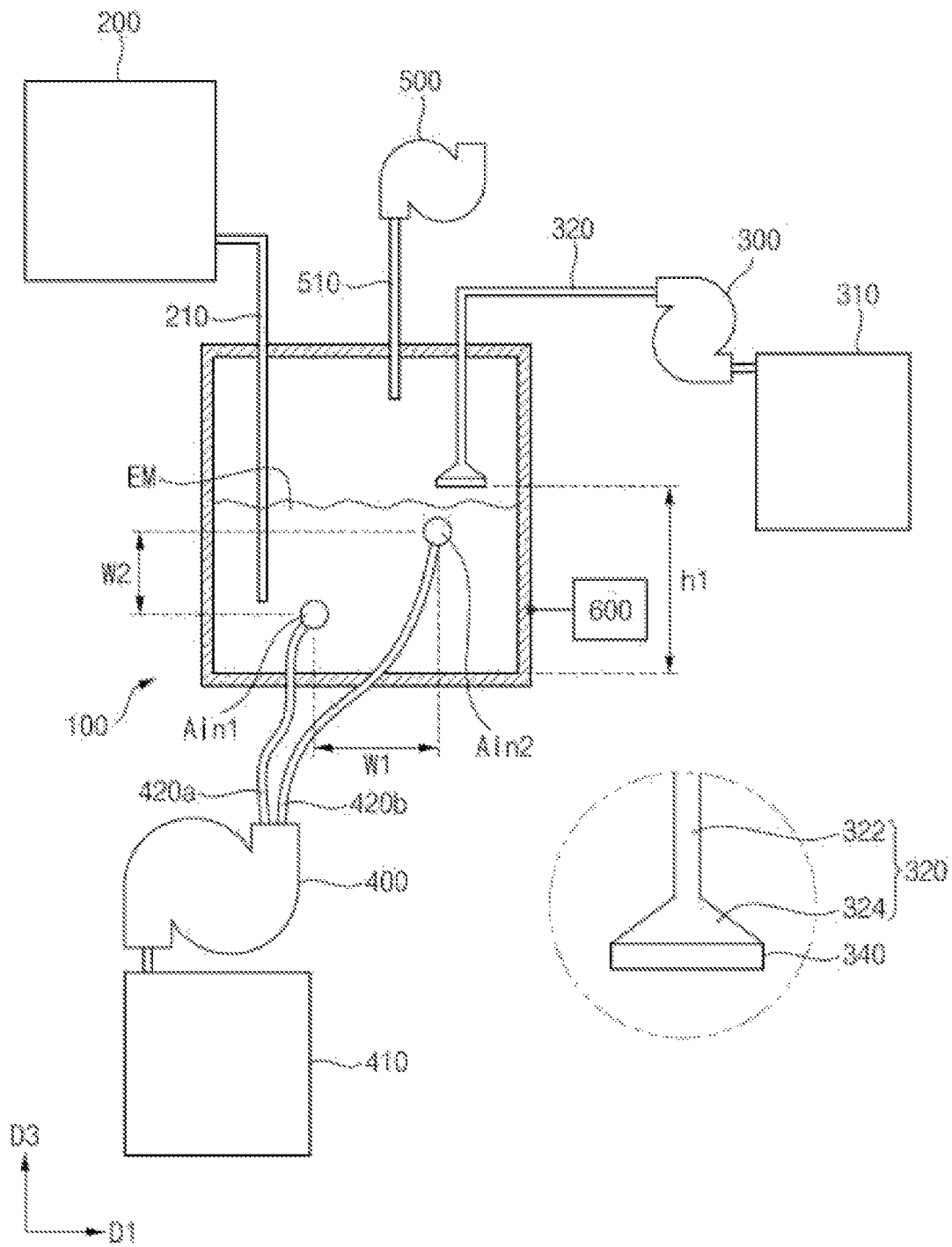
FIG. 1 is a schematic diagram illustrating a solvent removing apparatus according to an exemplary embodiment of the present invention.

Hereinafter, exemplary embodiments of the present invention will be described in more detail with reference to the drawings.

Since the present invention may have various changes and have various forms, specific exemplary embodiments are illustrated in the drawings and described in detail in the text. However, it is not intended to limit the present invention to the specific disclosed form, and it will be appreciated that the present invention includes all modifications, equivalences, or substitutions included in the spirit and the technical scope of the present invention.

FIG. 1 is a schematic diagram illustrating a solvent removing apparatus according to an exemplary embodiment of the present invention.

Referring to FIG. 1, the solvent removing apparatus may include a tank body 100, a liquid supply part 200, a liquid discharging part 300, a fluid supplying part 400, an exhaust part 500, and a heating part 600.

The tank body 100 may accommodate an emulsion including a first raw material of a continuous phase and a second raw material of a dispersed phase. The tank body 100 may include a wall body 110 forming a space for accommodating the emulsion EM therein. The tank body 100 may include a bottom portion formed on a plane formed by a first direction D1 and a second direction D2 perpendicular to the first direction D1, and include a lateral wall portion extending in a third direction D3 perpendicular to the first direction D1 and the second direction D2.

The first raw material may include purified water and surfactant. For example, the first raw material may be an aqueous solution in which polyvinyl alcohol (PVA) is dissolved as a surfactant in pure water.

The type of the surfactant is not particularly limited, and any biodegradable polymer solution may be used as long as the biodegradable polymer solution can help the forming of a dispersed phase of stable droplets in an aqueous solution phase that is a continuous phase. The surfactant may be preferably selected from the group consisting of methylcellulose, polyvinylpyrrolidone, carboxymethylcellulose, lecithin, gelatin, polyvinyl alcohol, polyoxyethylene sorbitan fatty acid ester, polyoxyethylene castor oil derivatives, and mixtures thereof.

The second raw material is an oil-phase solution, and may include an organic solvent, a biodegradable polymer dissolved therein, and a drug. The organic solvent is a solvent used to dissolve the biodegradable polymer, and may have water-immiscible properties. The type of organic solvent dissolving the biodegradable polymer is not particularly limited, but may be preferably selected from the group consisting of dichloromethane, chloroform, ethyl acetate, acetone, acetonitrile, dimethyl sulfoxide, dimethylformamide, methyl ethyl ketone, acetic acid, methyl alcohol, ethyl alcohol, propyl alcohol, benzyl alcohol, and a mixed solvent thereof.

The type of the biodegradable polymer is not particularly limited, but polyester may be preferably used, and in particular, the biodegradable polymer may be selected from the group consisting of polylactide, polyglycolide, poly(lactide-co-glycolide), poly(lactide-co-glycolide) glucose, polycaprolactone, and mixtures thereof.

The type of the drug is not particularly limited, and for example, the drug may be selected from antipsychotic drugs, such as dementia treatment drug, Parkinson's disease treatment, anticancer drugs, antianxiety drugs, antidepressants, tranquilizers, and psychotropic drugs; cardiovascular treatment agents, such as hyperlipidemia agents, antihypertensive agents, hypotensive agents, antithrombotic agents, vasodilators, and arrhythmias; gastrointestinal treatment agents, such as epilepsy treatment agent and anti-ulcer agent; hormonal drugs, such as rheumatoid treatment agent; antispasmodics; tuberculosis treatment agent; muscle relaxants agent; osteoporosis treatment agent; erectile dysfunction treatment agent; styptic; and sex hormones; diabetes treatment agent; antibiotic; antifungal agents; antiviral agents; antipyretic analgesic and anti-inflammatory agent; autonomic drug; corticosteroids; diuretics; antidiuretics; painkiller; anesthetic; antihistamines; antiprotozoal; anti-anemia agent; anti-asthma agent; antispasmodics; antidote; antimigraine; antiemetic; anti-Parkinson's drugs; antiepileptic drugs; antiplatelet agents; antitussive expectorant; bronchodilator; cardiotonic; immunomodulators; protein drugs; gene drugs; and mixtures thereof.

The foregoing kind of the drug is not particularly limited, and preferably, the drug may be selected from the group consisting of donepezil, memantine, rivastigmine, entecavir, lamivudine, rotigotine, ropinirole, bupivacaine, ropivacaine, meloxicam, buprenorphine, fentanyl, nimodipine, granisetron, triamcinolone, cytarabine, carmustine, tamsoleucine, polmacoxib, testosterone, estradiol, risperidone, paliperidone, olanzapine, aripiprazole, goserelin, leuprolide, tryptorelin, buserellin, naparelin, deslorrelin, octreotide, pasireotide, lanreotide, vapretide, exenatide, liraglutide, lixisenatide, semaglutide, salts thereof, and mixtures thereof.

The emulsion EM may be formed by various known methods by using the first raw material and the second raw material. For example, a method of mixing and stirring the first raw material and the second raw material, a microfluid method of forming microsphere droplets through a flow of a micro flow path, and the like may be used.

Further, in the exemplary embodiments of the present invention, the case has been described in which the dispersed phase of the emulsion EM includes the oil-phase solution and the continuous phase includes the aqueous-phase solution, but the present invention is not limited thereto. The case where the dispersed phase of the emulsion includes an aqueous-phase solution and the continuous phase includes an oil-phase solution is also possible, and in this case, the drug contained in the microspheres may include a hydrophilic therapeutic agent.

The liquid supply part 200 may supply a liquid into the tank body 100. The liquid supply part 200 may supply the liquid into the tank body 100 through a liquid supply pipe 210 passing through the wall body 110 of the tank body 100. The liquid may include a material that is the same as or similar to the continuous phase of the emulsion EM. For example, when the first raw material that is the continuous phase of the emulsion EM includes purified water and a surfactant, the liquid may include purified water.

The liquid supply pipe 210 may be extended toward the space in which the emulsion EM is accommodated from an upper portion of the tank body 100. A portion in which the liquid supply pipe 210 passes through the wall body 110 of the tank body 100 is formed in an upper portion of the tank body 100, so that there is little risk of the emulsion EM leaking to the portion through which the wall body 110 is penetrated.

The liquid discharge part 300 may discharge a part of the continuous phase of to the emulsion EM inside the tank body 100 to the outside of the tank body 100. The organic solvent existing in the dispersed phase may be sufficiently extracted and evaporated in the continuous phase by removing a part of the continuous phase including the organic solvent extracted from the dispersed phase of the emulsion EM and supplying a new aqueous solution (supplied by the liquid supply part 200) that is capable of replacing the removed continuous phase.

The solvent removing apparatus may further include a discharged liquid storage part 310 and a liquid discharge pipe 320. The liquid discharge pipe 320 may include a pipe portion 322, an expanded pipe portion 324, and a filter 340 formed in the expanded pipe portion 324. The discharge liquid storage part 310 is connected to the liquid discharge part 300 and store a part of the discharged continuous phase. One end of the pipe portion 322 may be connected to the liquid discharge part 300, and the other end may be connected to the expanded pipe portion 324. The pipe portion 322 may be extended toward the space in which the emulsion EM is accommodated from the upper portion of the tank body 100, so that the expanded pipe portion 324 may be formed at a first height h1 from the bottom portion of the tank body 100.

The emulsion EM is discharged to the outside of the tank body 100 through the filter 340 formed at a distal end of the expanded pipe portion 324, so that when the first height h1 is appropriately adjusted, it is possible to maintain a water level of the emulsion EM at an appropriate position. That is, the expanded pipe portion 324 is positioned at the first height h1 from the bottom portion of the tank body 100 and is in contact with a water level surface of the emulsion EM, thereby maintaining an appropriate volume of the emulsion EM inside the tank body 100.

The filter 340 is formed in the expanded pipe portion 324, so that only the continuous phase of the emulsion may be allowed to pass through the filter and the dispersed phase of the emulsion or the microspheres solidified from the dispersed phase may not be allowed to pass through the filter. For example, the filter 340 may have pores that have a size of ⅔ or less of the average size of the dispersed phase of the emulsion EM, and for example, the pore size of the filter 340 is about 10 μm (micrometer) level. As the filter 340, various known filters, such as a micro filter and a micro membrane, may be used.

In the meantime, according to the stirring of the emulsion EM, a number of bubbles may be generated on the water level surface of the emulsion EM. In particular, when the emulsion EM includes a surfactant as a constituent component, the degree of foaming may be increased. The bubbles generated on the water level surface of the emulsion (EM) make it difficult to check the current water level surface of the emulsion (EM), and in particular, when a sensor device, such as an optical sensor, is used to check the water level surface of the emulsion EM, the accuracy of the measurement is inevitably reduced. However, according to the present exemplary embodiment, simply by installing the expanded pipe portion 324 to be located at the first height h1 from the bottom portion of the tank body 100, it is easy to maintain a proper water level surface of the emulsion EM without a separate sensor device.

The fluid supply part 400 may supply a fluid to the emulsion EM accommodated inside the tank body 100. Through the supply of the fluid, the flow is formed in the emulsion EM to accelerate the extraction and the evaporation of the solvent in the continuous phase from the dispersed phase of the emulsion EM. The fluid is gas, and may be supplied to the emulsion EM in the form of gas bubbles.

The fluid supply part 400 may supply the fluid stored in the supplied fluid storage part 410 to the emulsion EM through a fluid supply means formed inside the tank body 100. Gas may be stored in the supplied fluid storage part 410, and nitrogen or air may be stored.

The fluid supply means includes a first fluid supply part Ain1 and a second fluid supply part Ain2, and the first fluid supply part Ain1 and the second fluid supply part Ain2 may be connected to the fluid supply part 400 through a first fluid supply pipe 420a and a second fluid supply pipe 420b, respectively.

Figure 2A:
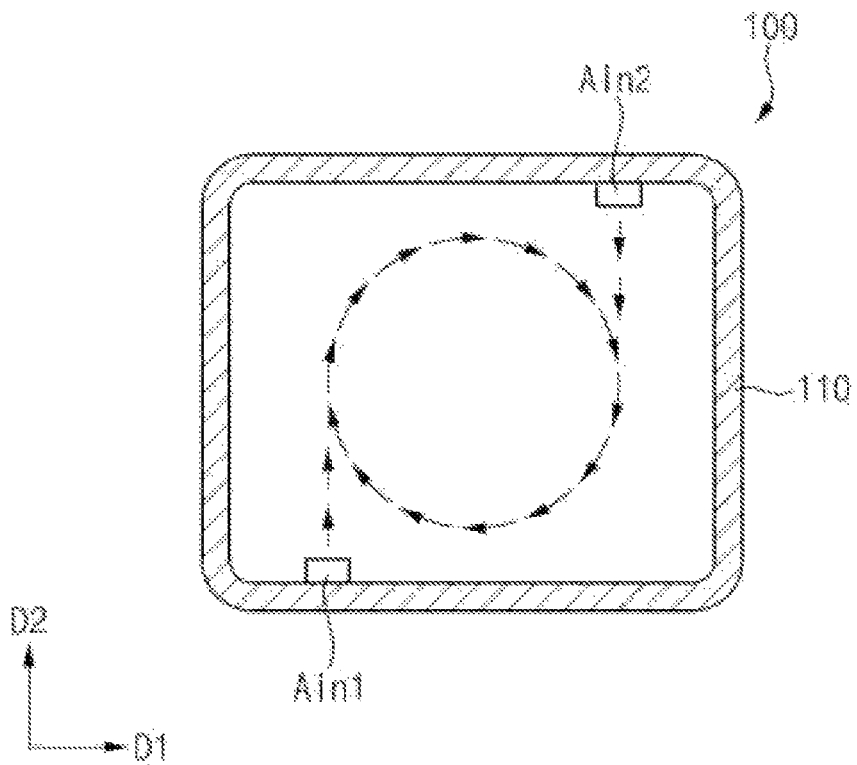
FIGS. 2A and 2B are planar cross-sectional views of the solvent removing apparatuses according to exemplary embodiments of the present invention.
Figure 2B:
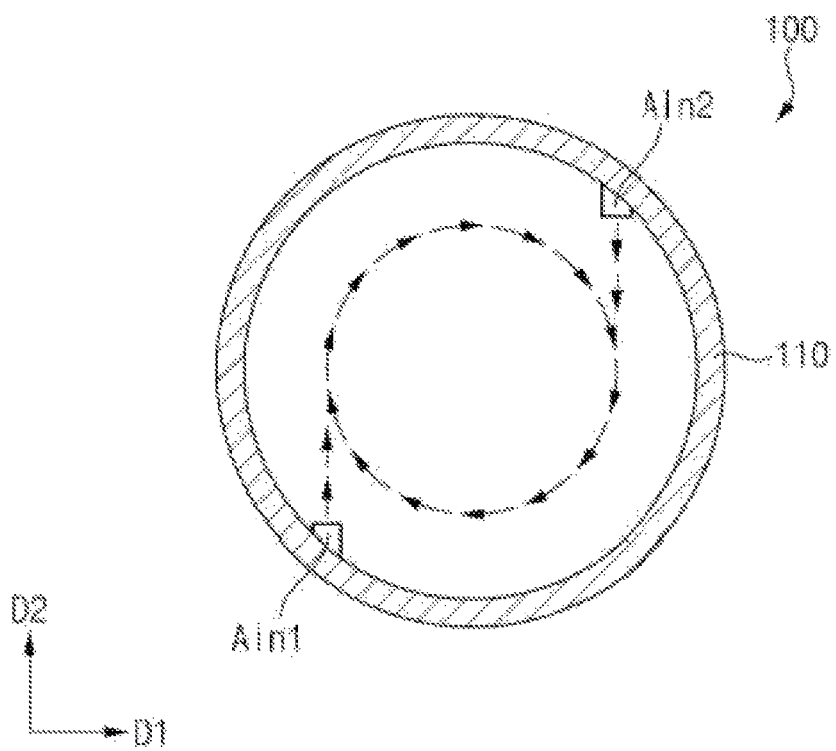

The first fluid supply part Ain1 and the second fluid supply part Ain2 are disposed while being spaced apart from each other inside the tank body, so that a rotational flow may be formed in the emulsion EM by the fluid supplied through the first fluid supply part Ain1 and the second fluid supply part Ain2 (see FIGS. 2A and 2B).

The fluid, that is, the gas bubbles, supplied to the emulsion EM through the fluid supply part 400 serves to stir the emulsion EM. Through this, the dispersed phases within the emulsion EM are prevented from sinking or sticking to each other to accelerate the extraction and the evaporation of the solvent. In addition, the gas bubbles within the emulsion EM are in contact with each other to maximize the extraction of the solvent from the dispersed phase. For example, an effect similar to the effect of purging nitrogen in addition to the emulsion stirred using a general stirrer may be realized through the present exemplary embodiment.

In fact, it was confirmed through experiments that the case of using gas bubbles was more effective than the case of extracting and evaporating the solvent using a physical stirrer.

When the emulsion including the organic solvent in the dispersed phase is maintained or stirred for a predetermined time at a temperature lower than a boiling point, the organic solvent of the continuous phase may be extracted from the biodegradable polymer solution in the form of droplets, which is a dispersed phase. A part of the organic solvent extracted in the continuous phase may be evaporated from a surface. As the organic solvent is extracted and evaporated from the biodegradable polymer solution in the form of droplets, the dispersed phase in the form of droplets may be solidified to form a microsphere. In this case, the extraction and the evaporation may be accelerated to by making the emulsion flow or heating the emulsion. For example, by forming a fluid flow in the emulsion, the solvent of the second raw material may be extracted and the extracted solvent may be removed by evaporating the extracted solvent.

The exhaust part 500 may serve to suck in the gas inside the tank body 100, and depressurize the inside of the tank body 100. Through this, the boiling point of the organic solvent is reduced, so that the organic solvent extracted in the continuous phase may be vaporized event at a low temperature. Further, the organic solvent gas extracted and evaporated from the dispersed phase of the emulsion EM may be discharged to the outside of the tank body 100 through the exhaust part 500. Through this, the partial pressure of the organic solvent within the tank body 100 is lowered, so that continuous extraction and evaporation of the solvent may be achieved.

The exhaust part 500 may suck in the gas inside the tank body 100 through the exhaust pipe 510 penetrating and inserted into the upper portion of the tank body 100.

The heating part 600 may heat the emulsion EM inside the tank body 100. The heating part 600 may have various known configurations that are capable of heating the inside of the tank body 100. The heating part 600 vaporize and remove the solvent by heating the emulsion EM to a boiling point, for example, 40 degrees, of the organic solvent or higher.

Although not illustrated, the solvent removing apparatus may further include a control unit controlling each configuration within the solvent removing apparatus to control the degrees of the supply of the fluid, the supply and the discharge of the liquid, and the exhaust to required degrees.

According to the present exemplary embodiment, the solvent removing apparatus includes a fluid supply part which supplies a fluid into the tank body to form a flow in the emulsion, and an exhaust part which discharges the gas inside the tank body to the outside of the tank, thereby easily extracting and evaporating the solvent even without an impeller or stirrer structure coupled to a shaft rotated by using a motor. Accordingly, the solvent removing apparatus has a simpler configuration that that of the structure in the related art, and may have an advantageous operation effect in sealing and the like for washing and sterilizing the inside of the tank body.

Further, the solvent removing apparatus further includes the liquid supply part which supplies the liquid into the tank body and the liquid discharge part which discharges a part of the continuous phase of the emulsion inside the tank body to the outside of the tank body, so that the solvent may be efficiently and continuously extracted and evaporated. Through this, it is possible to provide the efficient microsphere producing method by omitting or minimizing the subsequent separate filtering and cleaning operations after the solvent removing operation.

In the meantime, the method of recovering the microspheres from the continuous phase including the microspheres and cleaning the microspheres are not particularly limited, and the microspheres may be recovered by using a method, such as filtration and centrifugation, and then cleaning using water and the like may be additionally performed.

After the filtering and cleaning operation, the obtained microspheres are dried by using a general drying method to finally obtain the dried microsphere powder. The method of drying the microspheres is not limited, and may be performed by using a freezing drying method, a vacuum drying method, or a reduced pressure drying method.

Through the drying process of the microspheres, a final desired monodisperse biodegradable polymer-based microsphere powder is prepared, and then, a final product may be obtained by suspending the obtained microsphere powder in a suspension and filling an appropriate container, for example, a disposable syringe, with the suspended microsphere powder.

FIGS. 2A and 2B are planar cross-sectional views of the solvent removing apparatuses according to exemplary embodiments of the present invention.

Referring to FIGS. 1 to 2B, the solvent removing apparatus may include the tank body 100, the liquid supply part 200, the liquid discharging part 300, the fluid supplying part 400, the exhaust part 500, and the heating part 600.

The tank body 100 may accommodate an emulsion including a first raw material of a continuous phase and a second raw material of a dispersed phase. The tank body 100 may include a wall body 110 forming a space for accommodating the emulsion EM therein. The tank body 100 may include a bottom portion formed on a plane formed by a first direction D1 and a second direction D2 perpendicular to the first direction D1, and include a lateral wall portion extending in a third direction D3 perpendicular to the first direction D1 and the second direction D2.

The fluid supply part 400 may supply the fluid stored in the supplied fluid storage part 410 to the emulsion EM through a fluid supply means formed inside the tank body 100. The fluid supply means may include a first fluid supply part Ain1 and a second fluid supply part Ain2.

FIG. 2A illustrates an example of the case where a planar cross-sectional view of the tank body 100 has a quadrangular shape, and FIG. 2B illustrates an example of the case where a planar cross-sectional view of the tank body 100 has a circular shape, and the tank body 100 may have various shapes.

The first fluid supply part Ain1 and the second fluid supply part Ain2 may be formed to supply a fluid in different directions. That is, the first fluid supply part Ain1 may supply the fluid in the second direction D2, and the second fluid supply part Ain2 may supply the fluid in an opposite direction of the second direction D2.

The first fluid supply part Ain1 and the second fluid supply part Ain2 may be spaced apart from each other in the first direction D1, may be spaced apart from each other in the second direction D2, and may be spaced apart from each other in the third direction D3. Through this, within the tank body 100, the emulsion EM may form a three-dimensional rotational flow in the emulsion EM, and an optimal effect may be obtained with a small number of fluid supply parts (the gas supply pipes to which gas droplets are supplied). In the meantime, in the present exemplary embodiment, the fluid supply means includes two fluid supply parts, but the present invention is not limited thereto. Only one gas supply pipe of the fluid supply part through which the gas bubbles are supplied may be installed, and a plurality of three or more gas supply pipes may also be formed at various locations.

Figure 3:
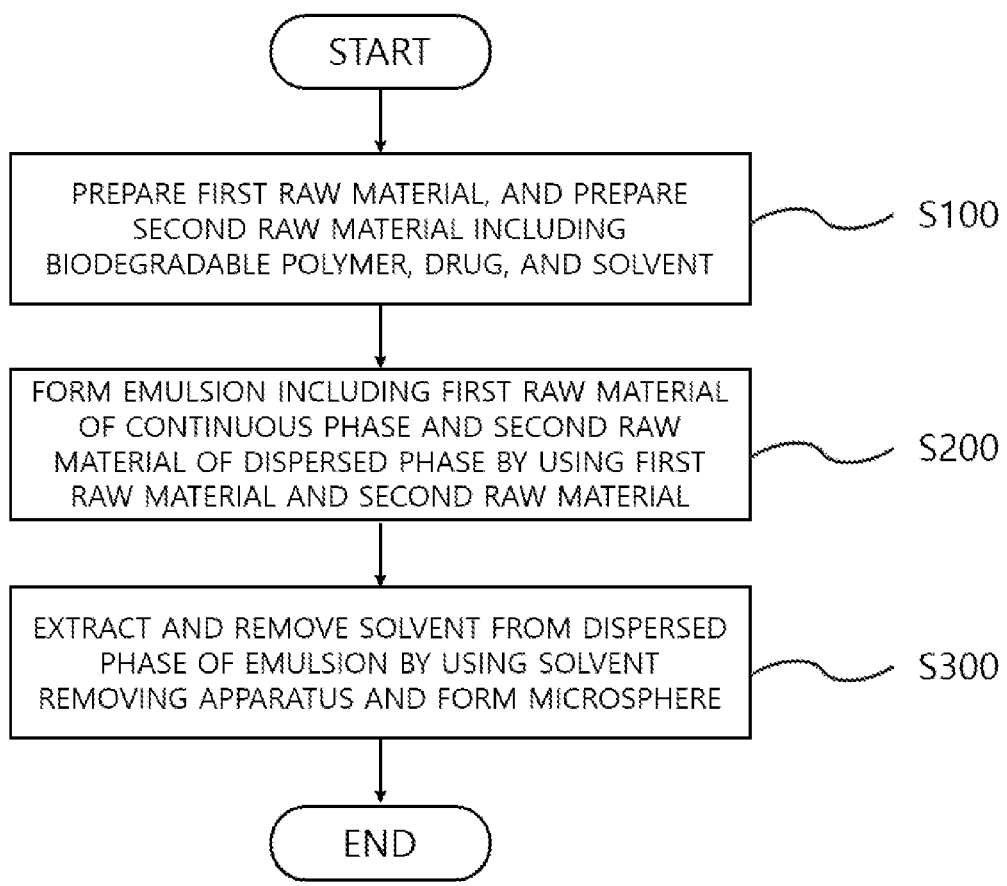
FIG. 3 is a flowchart illustrating a microsphere producing method using the solvent removing apparatus according to an exemplary embodiment of the present invention.

FIG. 3 is a flowchart illustrating a microsphere producing method using the solvent removing apparatus according to an exemplary embodiment of the present invention.

Referring to FIG. 3, the microsphere producing method is performed by using the solvent removing apparatus. The solvent removing apparatus includes a tank body, a fluid supply part for supplying a fluid into the tank body, and an exhaust part for discharging gas inside the tank body to the outside of the tank.

The microsphere producing method includes: preparing a first raw material and preparing a second raw material including a biodegradable polymer, a drug, and a solvent (S100); forming an emulsion including the first raw material of a continuous phase and the second raw material of a dispersed phase by using the first raw material and the second raw material (S200); and extracting and removing the solvent from the dispersed phase of the emulsion by using the solvent removing apparatus to form a microsphere (S300).

In the operation S100 of preparing the first raw material and preparing the second raw material including the biodegradable polymer, the drug, and the solvent, the first raw material and the second raw material may be prepared. The first raw material may include purified water and surfactant. The second raw material is an oil-phase solution, and may include an organic solvent, a biodegradable polymer dissolved therein, and a drug.

In the operation S200 of forming the emulsion including the first raw material of the continuous phase and the second raw material of the dispersed phase by using the first raw material and the second raw material, the emulsion may be formed by using the first raw material and the second raw material by various known methods. For example, a method of mixing and stirring the first raw material and the second raw material, a microfluid method of forming microsphere droplets through a flow of a micro flow path, and the like may be used. The emulsion includes the first raw material of the continuous phase and the second raw material of the dispersed phase.

In the operation S300 of extracting and removing the solvent from the dispersed phase of the emulsion by using the solvent removing apparatus to form the microsphere, a flow may be formed in the emulsion by supplying a fluid to the emulsion accommodated inside the tank body. The fluid is gas and may be supplied to the emulsion in the form of gas bubbles. Through this, the extraction of the solvent from the dispersed phase of the emulsion to the continuous phase and the evaporation of the extracted solvent may be accelerated. The gas may be nitrogen or air.

In the meantime, the solvent removing apparatus may further include the liquid supply part which supplies the liquid into the tank body and the liquid discharge part which discharges a part of the continuous phase of the emulsion inside the tank body to the outside of the tank body. The solvent existing in the dispersed phase may be sufficiently extracted and evaporated in the continuous phase by removing a part of the continuous phase including the organic solvent extracted from the dispersed phase of the emulsion and supplying a new aqueous solution (supplied by the liquid supply part) that is capable of replacing the removed continuous phase.

Further, the solvent removing apparatus may further include a heating part which heats the emulsion inside the tank body. By heating the emulsion at the temperature of the boiling point of the solvent or higher, the solvent may be vaporized and removed.

Through this, the dispersed phase in the form of droplets may be solidified to form a microsphere.

The microsphere producing method may further include cleaning and drying, or drying the formed microsphere and obtaining dried microsphere powder (S400). The solidified microsphere may be recovered by using a method, such as filtration and centrifugation, and then cleaning using water may be performed. After the filtering and cleaning operations, finally dried microsphere powder may be obtained by drying the obtained microspheres by using a general drying method. The method of drying the microspheres is not limited, and may be performed by using a freezing drying method, a vacuum drying method, or a reduced pressure drying method.

Through the drying process of the microspheres, the final desired monodisperse biodegradable polymer-based microsphere powder is prepared, and then, the obtained microsphere powder is suspended in a suspension and filled in an appropriate container, for example, a disposable syringe, to obtain a final product.

According to the present exemplary embodiment, the solvent removing apparatus includes a fluid supply part which supplies a fluid into the tank body to form a flow in the emulsion, and an exhaust part which discharges the gas inside the tank body to the outside of the tank, thereby easily extracting and evaporating the solvent even without an impeller or stirrer structure coupled to a shaft rotated by using a motor. Accordingly, the solvent removing apparatus has a simpler configuration that that of the structure in the related art, and may have an advantageous operation effect in sealing and the like for washing and sterilizing the inside of the tank body.

Further, the solvent removing apparatus further includes the liquid supply part which supplies the liquid into the tank body and the liquid discharge part which discharges a part of the continuous phase of the emulsion inside the tank body to the outside of the tank body, so that the solvent may be efficiently and continuously extracted and evaporated. Through this, it is possible to provide the efficient microsphere producing method by omitting or minimizing the subsequent separate filtering and cleaning operations after the solvent removing operation.

In the meantime, in the exemplary embodiments of the present invention, although the case where the dispersed phase of the emulsion includes the oil-phase solution and the continuous phase includes the aqueous-phase solution has been described, the present invention is not limited thereto. The case where the dispersed phase of the emulsion includes an aqueous-phase solution and the continuous phase includes an oil-phase solution is also possible, and in this case, the drug contained in the microspheres may include a hydrophilic therapeutic agent.

Although the present invention has been described with reference to the above exemplary embodiments, it will be understood by those skilled in the art that various modifications and changes can be made to the present invention without departing from the spirit and scope of the present invention as set forth in the claims below.

What is claimed is:

1. An apparatus for removing a solvent, the apparatus comprising:
   a tank body configured to accommodate an emulsion including a first raw material of a continuous phase and a second raw material of a dispersed phase;
   a fluid supply part configured to supply a fluid into the tank body and form a flow in the emulsion; and
   an exhaust part configured to discharge gas inside the tank body to the outside of the tank body,
   wherein the fluid supply part includes a first fluid supply part and a second fluid supply part, and
   the first fluid supply part and the second fluid supply part are disposed while being spaced apart from each other inside the tank body, so that a rotational flow is formed in the emulsion by the fluid supplied through the first fluid supply part and the second fluid supply part, and,
   wherein the first fluid supply part and the second fluid supply part are configured to supply the fluids in different directions,
   the tank body has a bottom portion formed on a plane formed by a first direction and a second direction perpendicular to the first direction, and a lateral wall portion extended in a third direction perpendicular to the first direction and the second direction, and
   the first fluid supply part and the second fluid supply part are spaced apart from each other in the first direction, are spaced apart from each other in the second direction, and are spaced apart from each other in the third direction.

2. The apparatus of claim 1, wherein the fluid supply part supplies gas bubbles to the emulsion accommodated inside the tank body.

3. The apparatus of claim 1, wherein the exhaust part sucks in the gas inside the tank body and depressurizes the inside of the tank body.

4. The apparatus of claim 1, further comprising:
   a liquid supply part configured to supply a liquid into the tank body,
   wherein the liquid includes a main ingredient of the continuous phase.

5. The apparatus of claim 4, further comprising:
   a liquid discharge part configured to discharge a part of the continuous phase of the emulsion inside the tank body to the outside of the tank body.

6. An apparatus for removing a solvent, the apparatus comprising:
   a tank body configured to accommodate an emulsion including a first raw material of a continuous phase and a second raw material of a dispersed phase;
   a fluid supply part configured to supply a fluid into the tank body and form a rotational flow in the emulsion;
   an exhaust part configured to discharge gas inside the tank body to the outside of the tank body; and
   a liquid discharge part configured to discharge a part of the continuous phase of the emulsion inside the tank body to the outside of the tank body,
   wherein the liquid discharge part has a pipe portion extended into the tank body and an expanded pipe portion connected to a distal end of the pipe portion, and
   the expanded pipe portion is located at a first height from a bottom portion of the tank body, and is in contact with a water level surface of the emulsion to maintain an appropriate volume of the emulsion inside the tank body.

7. The apparatus of claim 6, wherein a filter is formed in the expanded pipe portion, so that only the continuous phase of the emulsion passes through the filter and the dispersed phase of the emulsion or microspheres solidified from the dispersed phase do not pass through the filter.

8. The apparatus of claim 1, wherein the first raw material includes purified water and surfactant, and the second raw material includes an organic solvent, a biodegradable polymer, and a drug.

9. The apparatus of claim 1, further comprising:
   a heating part configured to heat the emulsion inside the tank body.

* * * * *